(12) United States Patent
Shan et al.

(10) Patent No.: US 12,408,938 B2
(45) Date of Patent: Sep. 9, 2025

(54) NEOSTOMY APPARATUS

(71) Applicant: LIFETECH SCIENTIFIC (SHENZHEN) CO., LTD., Guangdong (CN)

(72) Inventors: Shuo Shan, Shenzhen (CN); Huiqiang Tang, Shenzhen (CN); Peng Liu, Shenzhen (CN)

(73) Assignee: LIFETECH SCIENTIFIC (SHENZHEN) CO., LTD., Shenzhen (CN)

( * ) Notice: Subject to any disclaimer, the term of this patent is extended or adjusted under 35 U.S.C. 154(b) by 537 days.

(21) Appl. No.: 17/786,800

(22) PCT Filed: Nov. 25, 2020

(86) PCT No.: PCT/CN2020/131491
§ 371 (c)(1),
(2) Date: Jun. 17, 2022

(87) PCT Pub. No.: WO2021/129288
PCT Pub. Date: Jul. 1, 2021

(65) Prior Publication Data
US 2023/0043955 A1 Feb. 9, 2023

(30) Foreign Application Priority Data
Dec. 26, 2019 (CN) .................. 201911369159.X

(51) Int. Cl.
*A61B 17/295* (2006.01)
*A61B 17/00* (2006.01)
*A61B 17/29* (2006.01)

(52) U.S. Cl.
CPC ........ *A61B 17/295* (2013.01); *A61B 17/2909* (2013.01); *A61B 2017/00367* (2013.01); *A61B 2017/2948* (2013.01); *A61B 2217/005* (2013.01)

(58) Field of Classification Search
CPC .............. A61B 17/295; A61B 17/2909; A61B 2017/00367; A61B 2017/2948;
(Continued)

(56) References Cited

U.S. PATENT DOCUMENTS

2004/0230169 A1* 11/2004 Felix .................... A61M 1/7411
604/317
2011/0034804 A1 2/2011 Hubregtse et al.

FOREIGN PATENT DOCUMENTS

CN 202490022 U 10/2012
CN 103370019 A * 10/2013 ....... A61B 17/22031
(Continued)

OTHER PUBLICATIONS

International Search Report mailed Feb. 25, 2021, in corresponding to International Application No. PCT/CN2020/131491; 6 pages (with English Translation).
(Continued)

*Primary Examiner* — Shaun L David
*Assistant Examiner* — Rachael L Geiger
(74) *Attorney, Agent, or Firm* — Maier & Maier, PLLC

(57) ABSTRACT

A neostomy apparatus, including a grasping device, a cutting device and a control handle. The control handle includes a housing and a manipulation portion disposed in the housing, the manipulation portion can move axially relative to the housing; the grasping device or the cutting device includes an elongated member, and the manipulation portion drives the elongated member to move axially; the elongated member is partially located in the housing, and a first limiting
(Continued)

structure is further disposed in the housing, the first limiting structure has a groove or a through hole, and a portion of the elongated member located in the housing is at least partially disposed in the groove or the through hole of the first limiting structure.

20 Claims, 7 Drawing Sheets

(58) Field of Classification Search
CPC ........ A61B 2217/005; A61B 17/32056; A61B 2017/00247; A61B 2017/2926; A61B 2017/306; A61B 17/320016; A61B 17/00234; A61B 17/3209; A61B 2017/00243
See application file for complete search history.

(56) References Cited

FOREIGN PATENT DOCUMENTS

| | | | |
|---|---|---|---|
| CN | 106420004 | A | 2/2017 |
| CN | 107343814 | A | 11/2017 |
| CN | 208582496 | U | 3/2019 |
| CN | 109984809 | A | 7/2019 |
| CN | 209153782 | U | 7/2019 |
| CN | 110368062 | A | 10/2019 |
| WO | WO-2019128772 | A1 * | 7/2019 ......... A61B 17/3209 |

OTHER PUBLICATIONS

Notification to Grant Patent Right for Invention issued Dec. 26, 2022, in corresponding Chinese Application No. 201911369159.X, 3 pages.
Second Office Action issued Aug. 3, 2022, in corresponding Chinese Application No. 201911369159.X, 42 pages.
First Office Action issued Oct. 26, 2021, in corresponding Chinese Application No. 201911369159.X, 27 pages.
The Second Office Action issued on Aug. 3, 2022, in corresponding Chinese Application No. 201911369159.X, 26 pages.
Office Action issued on Feb. 7, 2023, in corresponding Indian Application No. 202217041908, 7 pages.
Extended Search Report issued on Nov. 28, 2023, in corresponding European Application No. 20907149.7, 7 pages.

* cited by examiner

NEOSTOMY APPARATUS

TECHNICAL FIELD

The embodiments relate to the field of medical apparatuses, in particular to a neostomy apparatus.

BACKGROUND

Heart failure (referred to as "cardiac failure") is a group of complex clinical syndromes caused by ventricular filling or impaired ejection function due to any heart structural or functional abnormality, which is mainly manifested as dyspnea and asthenia (limited exercise tolerance), and fluid retention (pulmonary congestion and peripheral edema) clinically. Heart failure, as a severe stage developed from various heart diseases, is becoming the most important cardiovascular disease throughout the world.

Heart failure can be divided into diastolic heart failure and systolic heart failure. Diastolic heart failure refers to a congestion syndrome of pulmonary circulation and systemic circulation caused by the decrease of ventricular filling volume and the increase of filling pressure due to the decrease of ventricular relaxation and compliance in case of normal ventricular contraction functions. Diastolic heart failure will result in increased pressure in the left atrium and pulmonary veins, hindering the normal flow of oxygen bearing blood.

Currently, there are a few of methods for treating diastolic heart failure patients. Clinical data show that a small hole is opened on the interatrial septum of a diastolic heart failure patient to form a left-to-right shunt, which is beneficial to reducing the pressure of the heart failure patient in the left atrium. To open a small hole on interatrial septum requires a simple operation of the neostomy apparatus; especially the handle accords with the ergonomics and the control mechanism on the handle is simple.

SUMMARY

The embodiments provide a neostomy apparatus which is simple in construction and manipulation.

The embodiments provide a neostomy apparatus, including a grasping device, a cutting device and a control handle; where the control handle includes a housing and a manipulation portion disposed in the housing, the manipulation portion may axially move relative to the housing; the grasping device or the cutting device includes an elongated member, and the manipulation portion drives the elongated member to move axially; the elongated member is partially located in the housing, and a first limiting structure is further disposed in the housing, the first limiting structure has a groove or a through hole, and a portion of the elongated member located in the housing is at least partially disposed in the groove or the through hole of the first limiting structure.

In an embodiment, a proximal end of the first limiting structure is close to a distal end of the manipulation portion.

In an embodiment, the grasping device further includes a catheter body, where the elongated member is disposed to pass through the catheter body, and a proximal end of the catheter body is connected to the housing; and the housing is provided with a sealing assembly; the sealing assembly is located at the distal end of the housing and is sealingly connected to the proximal end of the catheter body, and the catheter body may be communicated with a negative pressure source through the sealing assembly, such that a negative pressure is formed in the catheter body under the action of the negative pressure source.

In an embodiment, the sealing assembly includes a hollow pipe body and a sealing member connected at both ends of the hollow pipe body; a vent hole is opened on a sidewall of the hollow pipe body, and the negative pressure source is communicated with the vent hole via a hose.

In an embodiment, the manipulation portion is connected with a second limiting structure; the second limiting structure may house the elongated member and is coaxial with the first limiting structure; a proximal end of the second limiting structure and a proximal end of the elongated member are fixed on the manipulation portion; a distal end of the second limiting structure is inserted into the groove or the through hole of the first limiting structure and may move axially relative to the first limiting structure under the action of the manipulation portion.

In an embodiment, a linear guide rail is fixedly disposed in the housing; the manipulation portion is slidably disposed on the linear guide rail; one or more arc-shaped grooves are disposed on a side of the linear guide rail; an elastic member and a ball are disposed in the manipulation portion; the ball is elastically abutted against one side of the linear guide rail opened with the arc-shaped groove under the action of the elastic member; and when the manipulation portion moves until the ball is opposite to the arc-shaped groove along the linear guide rail, partial structures of the ball are abutted into the arc-shaped groove.

In an embodiment, the neostomy apparatus further includes a conductive structure and a conductive interface disposed at a proximal end portion of the housing; the conductive structure always keeps electric connection with the manipulation portion and the conductive interface when the manipulation portion moves axially.

In an embodiment, the housing is provided with a conductive sliding rail, and a proximal end of the conductive sliding rail is connected to the conductive structure; and the manipulation portion is slidably connected to the conductive sliding rail, and the manipulation portion may move axially relative to the conductive sliding rail.

In an embodiment, the conductive structure includes a conductive elastic piece, and the conductive elastic piece is disposed at a sliding connection portion between the manipulation portion and the conductive sliding rail; when the manipulation portion moves axially along the conductive sliding rail, the conductive elastic piece is always abutted against the conductive sliding rail.

In an embodiment, the manipulation portion includes a sliding block and a pushing member; the sliding block is slidably disposed in the housing and is connected to the proximal end of the elongated member; the pushing member is connected to the sliding block, and partial structures of the pushing member are exposed to the housing, and the pushing member may move axially relative to the housing, such that the sliding block drives the elongated member to move axially.

The embodiments provide a neostomy apparatus, including a control handle; the control handle adsorbs a tissue at a position which requires neostomy by negative pressure generated by the catheter body in communication with a negative pressure source. Moreover, a first manipulation portion is utilized to drive a push rod to move axially in the catheter body such that a grasping portion connected to a distal end of the push rod is manipulated to grasp the tissue sucked into the catheter body, thereby facilitating the subsequent cutting and neostomy conducted on the tissue sucked into the catheter body by a second manipulation portion and a third manipulation portion. Moreover, buckle-proof or anti-buckling cannulas are sleeved on a push rod, a traction fiber and a control fiber of the cutting device.

DETAILED DESCRIPTION OF THE EMBODIMENTS

Figure 1:
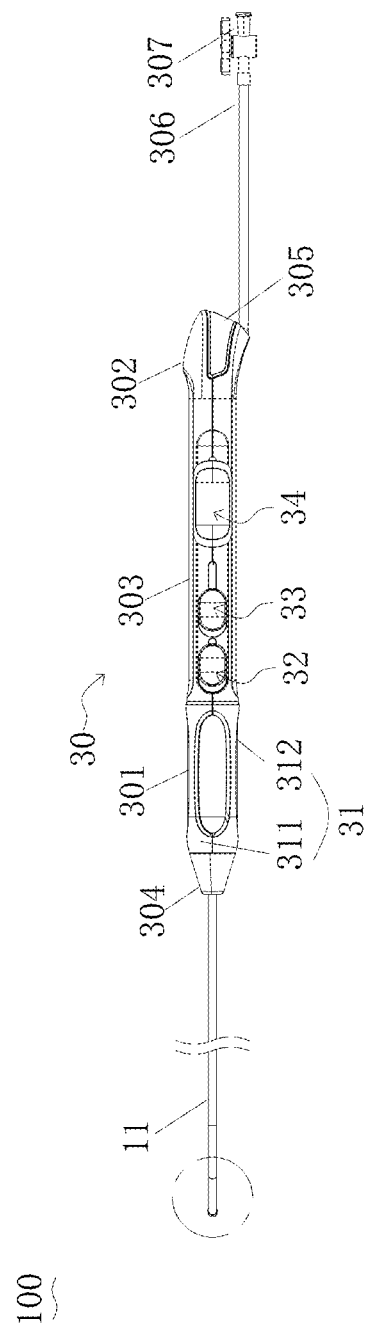
FIG. 1 is a schematic diagram illustrating a structure of a neostomy apparatus according to an embodiment of the embodiments.

For the convenience of understanding the embodiments, the embodiments will be described more comprehensively below with reference to relevant drawings.

Implementations of the embodiments are set forth in the drawings. However, the embodiments may be implemented in many different forms, but are not limited to the embodiments described herein. On the contrary, these embodiments are provided such that the embodiments are understood more thoroughly and comprehensively.

It can be understood that the terms "distal end" and "proximal end" are used as nouns of locality which are customary terms in the field of medical apparatus. The "distal end" denotes an end away from the operator during operation, and "proximal end" denotes an end close to the operator during operation. The axial direction refers to a direction parallel to the line of centers between the distal center and the proximal center of the medical apparatus; the radial direction refers to a direction perpendicular to the above axial direction.

Figure 2:
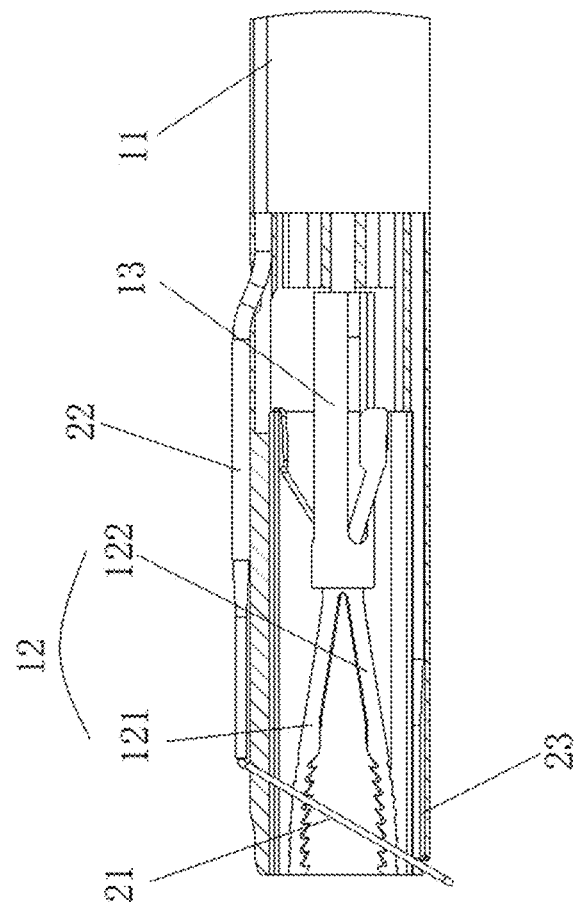
FIG. 2 is a partially enlarged schematic diagram illustrating an internal structure of the neostomy apparatus shown in FIG. 1.

Referring to FIGS. 1 and 2, the neostomy apparatus 100 provided by the embodiments includes a grasping device, a cutting device 20 and a control handle 30. Both the grasping device and the cutting device include an elongated member partially located within the control handle. The elongated member may include a push rod, a traction firer, and a control firer.

The grasping device includes a catheter body 11, a grasping portion 12 and a push rod 13. A proximal end of the catheter body 11 is connected to the control handle 30; the grasping portion 12 is disposed in the catheter body 11 and located at the distal end of the catheter body 11; a distal end portion of the push rod 13 is sleeved on the grasping portion 12, and the push rod 13 may move axially in the catheter body 11, so as to control the grasping portion 12 to perform a grasping operation.

The catheter body 11 has a hollow tubular structure which may be communicated with a negative pressure source to form negative pressure in the catheter body 11 under the action of the negative pressure source. Thus, a tissue of interatrial septum is absorbed by the negative pressure formed in the catheter body 11. The grasping portion 12 at the distal end of the catheter body 11 may grasp the tissue of human interatrial septum sucked into the lumen of the catheter body 11 by the neostomy apparatus 100 when it moves axially on the push rod 13.

The grasping portion 12 includes at least two oppositely disposed clamping jaws 121 and 122 which are fixed inside the distal end of the catheter body 11. A distal end portion of the push rod 13 is sleeved on the grasping portion 12, and thus, the push rod 13 may manipulate the opening or closure of the clamping jaws 121 and 122 in the grasping portion 12 when the push rod 13 moves axially relative to the catheter body 11, thus achieving a clamping action.

The cutting device 20 includes a cutting portion 21, a traction fiber 22 and a control fiber 23. The cutting portion 21 is disposed at the distal end of the catheter body 11 and partially surrounds the outer wall at an opening portion of the distal end of the catheter body 11. The cutting portion 21 is configured for cutting the tissue of human interatrial septum sucked into the lumen of the catheter body 11 by the neostomy apparatus 100. Both the distal ends of the traction fiber 22 and the control fiber 23 are connected to the cutting portion 21.

A first limiting structure, a push rod, a traction fiber and a control fiber are all partially located in the housing of the handle, and the portions located in the housing are all at least partially disposed in the groove or through hole of the first limiting structure. The structure is described in detail below.

A control handle 30 is used for manipulating the grasping device 10 of the neostomy apparatus 100 for gripping and is further used for the cutting device 20 of the neostomy apparatus 100 for cutting.

Figure 3:
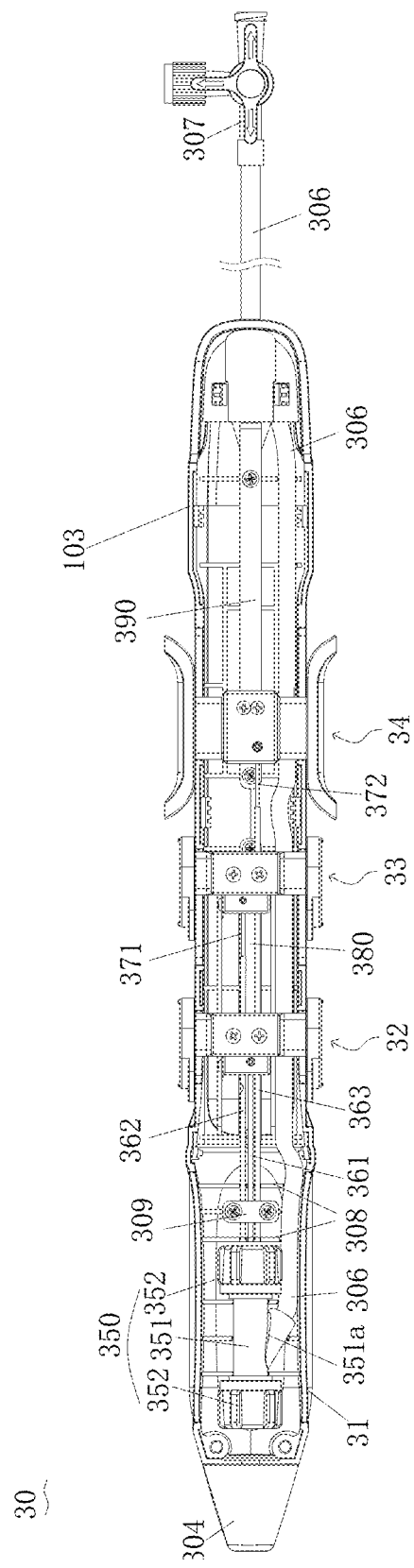
FIG. 3 is a schematic diagram illustrating an internal structure of a control handle of the neostomy apparatus according to an embodiment.

In combination with FIGS. 1 and 3, the control handle 30 includes a housing 31 and a manipulation portion disposed within the housing 31, and the manipulation portion manipulates the elongated member to move axially. The manipulation portion may particularly include a first manipulation portion 32, a second manipulation portion 33 and a third manipulation portion 34. The manipulation portion includes a sliding block and a pushing member; the sliding block is slidably disposed in the housing and connected to the proximal end of the elongated member; the pushing member is connected to the sliding block, and partial structures of the pushing member are exposed to the housing, and the pushing member may move axially relative to the housing, such that the sliding block drives the elongated member to move axially. In addition, an opening is opened on a sidewall of the housing, and a portion of the pushing member is exposed to the housing through the opening, and the opening has a certain length along the axial direction of the housing, and the axial length of the opening limits the axial moving range of the pushing member.

The proximal end of the catheter body 11 is connected to the housing 31, and a sealing assembly 350 is disposed in the housing 31; the sealing assembly 350 is located at the distal end of the housing 31 and is sealingly connected to the proximal end of the catheter body 11, such that after the catheter body 11 is in communication with the negative pressure source, the catheter body 11 may generate a negative pressure better under the action of the negative pressure source, so as to effectively suck the tissue of human interatrial septum into the lumen of the catheter body 11 for the subsequent grasping operation of the grasping device and the cutting operation of the cutting device 20.

Figure 5:
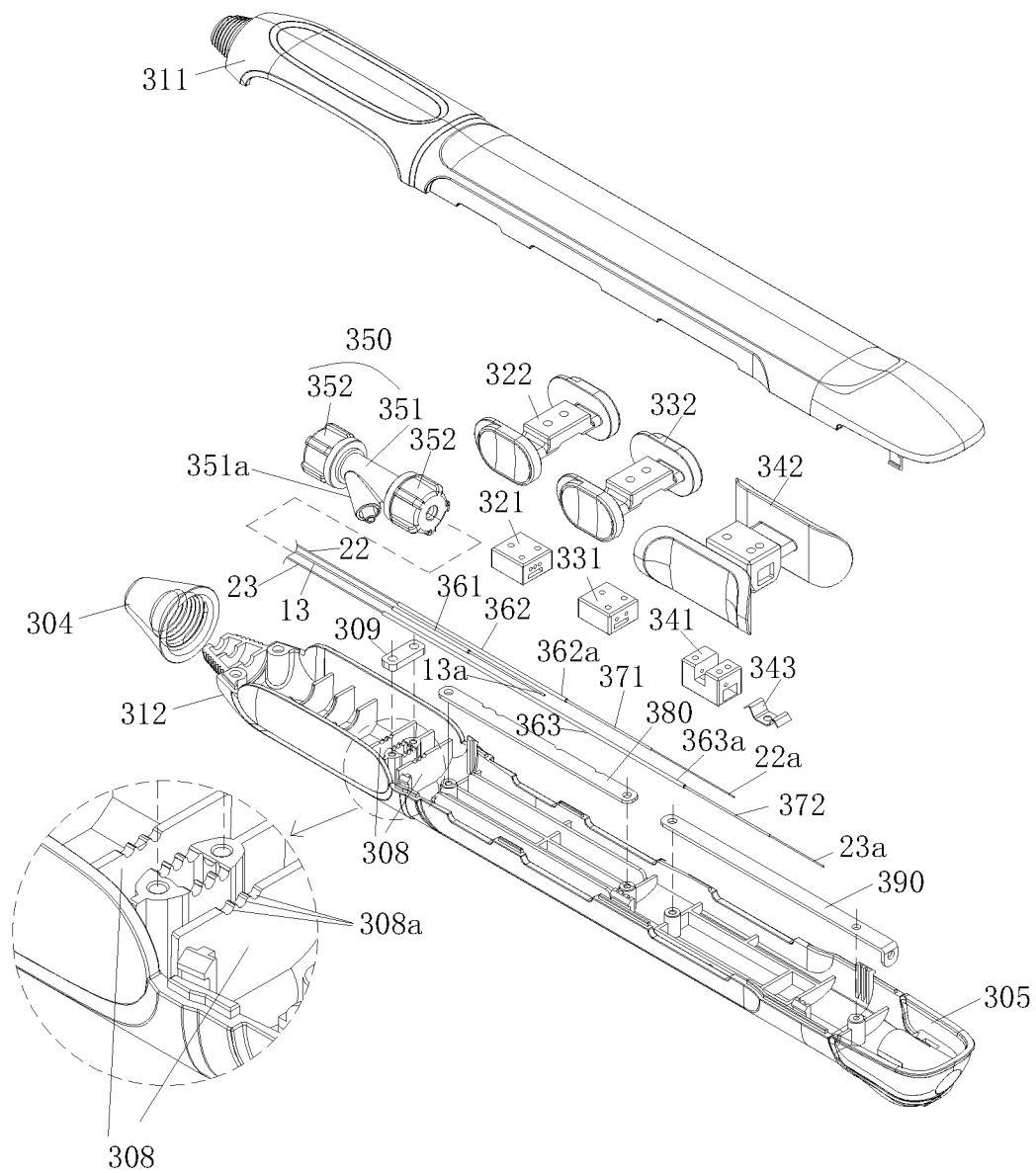
FIG. 5 is an exploded diagram of the control handle of the neostomy apparatus shown in FIG. 3.

As shown in FIG. 5, the sealing assembly 350 includes a hollow pipe body 351 and a sealing member 352 connected at two ends of the hollow pipe body 351; a vent hole 351a is opened on a sidewall of the hollow pipe body 351; and the negative pressure source is communicated with the vent hole 351a via a hose 306. Partial sections of the hose 306 may be disposed in the housing 31 and may be connected to an external negative pressure source via a three-way valve 307 after being led out from the housing 31, such that the three-way valve 307 may regulate the negative pressure source to act on the catheter body 11, and accordingly, the catheter body 11 may adsorb the tissue of human interatrial septum with a suitable negative pressure.

With continuing reference to FIG. 5, the housing 31 includes a first housing 311 and a second housing 312 which may be fastened together by a buckle, a screw or a glue bonding way. The distal end of the housing 31 may be tightly locked by a head cover 304. For example, when the first housing 311 and the second housing 312 are buckled together, the distal end thereof forms an external thread, and the head cover 304 is in threaded fit connection to the distal end of the housing 31, thereby locking the first housing 311 and the second housing 312 together and preventing the first housing 311 and the second housing 312 from loosening.

In some embodiments, the proximal end of the housing 31 may enclose a connection port of a radio frequency probe in the form of a trailing housing 305, such that the neostomy apparatus 100 is connected to an external high frequency equipment through the port. The neostomy apparatus 100 and a negative plate on the body surface form a current loop in operation, thereby satisfying the power-on needs of the cutting device 20 for operation.

It may be understood that the proximal end of the housing 31 refers to the end where the housing 31 faces the operator during handling and using, after being assembled to the neostomy apparatus.

With continuing reference to FIGS. 1 and 3, the housing 31 may be divided into a distal end section 301, a proximal end section 302, and a body section 303 connected between the distal end section 301 and the proximal end section 302 when the control handle 30 is manipulated. The distal section 301 may serve as a holding area for stabilizing the neostomy apparatus 100 during operation. An arc-shaped convex structure may be formed on an upper surface of the proximal section 302 to press against the palm to manipulate the control handle 30. For example, a first manipulation portion 32, a second manipulation portion 33 and a third manipulation portion 34 are distributed on the body section 303, used for manipulating the grasping device 10 and the cutting device 20, respectively. In other embodiments, the distribution position, i. e., the order, of the first manipulation portion 32, the second manipulation portion 33, and the third manipulation portion 34 is not limited in the housing 31 as long as these portions are adapted to the corresponding manipulation requirements only.

The first manipulation portion 32, the second manipulation portion 33 and the third manipulation portion 34 are respectively used for manipulating the axial movement of the push rod 13, the traction fiber 22 and the control fiber 23 in the catheter body 11, respectively, as an example, to further describe the structure of the manipulation handle.

Figure 4:
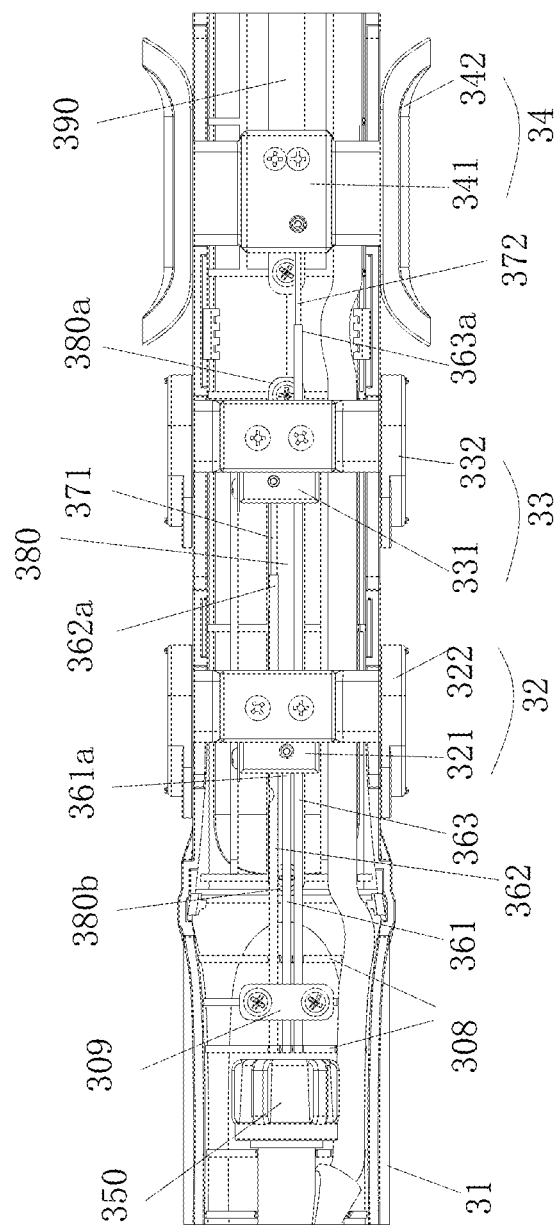
FIG. 4 is a partial schematic diagram illustrating an internal structure of the control handle of the neostomy apparatus shown in FIG. 3.

For example, in combination with FIGS. 3 to 5, the first manipulation portion 32 is connected to the proximal end 13a of the push rod 13 and is configured for driving the push rod 13 to move axially relative to the catheter body 11, such that the grasping portion 12 opens or closes under the axial movement of the push rod 13, thereby achieving the grasping manipulation of the grasping portion 12 via the first manipulation portion 32.

The second manipulation portion 33 is connected to the proximal end 22a of the traction fiber 22 and is configured for driving the traction fiber 22 to move axially in the catheter body 11. Since the traction fiber 22 is connected to the cutting portion 21 of the cutting device 20, the second manipulation portion 33 drives the traction fiber 22 to move axially in the catheter body 11, such that the cutting portion 21 may be suspended at the distal end of the catheter body 11 transformed from a tight state bound to the catheter body 11. Accordingly, the third manipulation portion 34 is connected with the proximal end 23a of the control fiber 23 and is configured for driving the control fiber 23 to move axially in the catheter body 11, thus holding the control fiber 23 into the catheter body 11.

In some embodiments, the traction fiber 22 and the control fiber 23 are symmetrically disposed on the wall of the catheter body 11 to exert an axial push-pull force on the opposite sides of the cutting portion 21 connected on the distal ends of the traction fiber 22 and the control fiber 23. In other embodiments, the traction fiber 22 and the control fiber 23 may also be disposed asymmetrically as long as it is ensured that the cutting portion 21 may be manipulated by the axial movement of the traction fiber 22 and the control fiber 23 in the catheter body 11. Therefore, the cutting portion 21 cuts the tissue of human interatrial septum sucked into the catheter body 11.

In some embodiments, the first limiting structure includes a cannula. For example, a first sleeve pipe 361 is fixedly disposed between the sealing assembly 350 and the first manipulation portion 32 in the housing 31; and the push rod 13 may be movably disposed to pass through the first sleeve pipe 361 axially, such that when the first manipulation portion 32 drives the push rod 13 to move towards the distal end due to the guiding effect of the first sleeve pipe 361 on the push rod 13, the push rod 13 is not easily bent due to the radial constraint of the first sleeve pipe 361, thereby improving the manipulation reliability.

It may be understood that the first sleeve pipe 361 serves as a limiting structure to produce a restraining effect in the radial direction when the push rod 13 moves in the axial direction, and the structure is configured to adapt to the first manipulation portion 32 such that the push rod 13 is driven to move axially, thereby manipulating the grasping portion 12 for grasping operation. Further, the configuration of the first sleeve pipe 361 does not interfere with the first manipulation portion 32 to manipulate the push rod 13 to move axially. For example, in some embodiments, the proximal end surface of the first sleeve pipe 361 just contacts the side on which the distal end of the first manipulating portion 32 is located when the push rod 13 is manipulated by the first manipulation portion 32 to move axially toward the distal end to a limiting position. In another example, in other embodiments, there is an interval or gap between the proximal end surface of the first sleeve pipe 361 and the side on which the distal end of the first manipulation portion 32 is located when the push rod 13 is manipulated by the first manipulation portion 32 to move axially toward the distal end to a limiting position. Whether the proximal end surface of the first sleeve pipe 361 is just in contact with or has a gap with the side on which the distal end of the first manipulation portion 32 is located, it is ensured that the first sleeve pipe 361 will not interfere with the movement of the first manipulation portion 32 towards the distal end when the push rod 13 is driven by the first manipulation portion 32 to manipulate the grasping portion 12 for operation.

With continuing reference to FIGS. 3 and 5, in some embodiments, a second sleeve pipe 362 and a third sleeve pipe 363 are fixedly disposed in the housing 31; distal ends of the second sleeve pipe 362 and the third sleeve pipe 363 are respectively fixed to the proximal end of the sealing assembly 350. The traction fiber 22 may be axially disposed to pass through the second sleeve pipe 362 movably, and the control fiber 23 may be axially disposed to pass through the third sleeve pipe 363 movably, such that the second sleeve pipe 362 and the third sleeve pipe 363 may have a better radial restraining effect on the traction fiber 22 and the control fiber 23, respectively. Thereby, the above configuration prevents the traction fiber 22 and the control fiber 23 from being easily bent under the pushing force of the second manipulation portion 33 and the third manipulation portion 34.

Two or more spaced supporting sheets 308 are disposed in the housing 31 at a position near the distal end; the supporting sheets 308 are fixed on the inner surface of the housing 31. Ports 308a are opened on the setting paths of the first sleeve pipe 361, the second sleeve pipe 362 and the third sleeve pipe 363, such that the first sleeve pipe 361, the second sleeve pipe 362 and the third sleeve pipe 363 are located in the corresponding ports 308a, thus stably fixing the first sleeve pipe 361, the second sleeve pipe 362 and the third sleeve pipe 363 in the housing 31 by the ports 308a.

The ports 308a may be a circular arc groove having a diameter comparable to or slightly smaller than that of the first sleeve pipe 361, the second sleeve pipe 362 and the third sleeve pipe 363.

A gland 309 may be disposed between the supporting sheets 308 to further fasten the first sleeve pipe 361, the second sleeve pipe 362, and third sleeve pipe 363.

For example, both ends of the gland 309 are respectively fixed to the housing 31 by buckling, welding, glue bonding or screws, or the like. The gland 309 is pressed on the first sleeve pipe 361, the second sleeve pipe 362 and the third sleeve pipe 363, so as to achieve a better stabilizing effect and prevent the first sleeve pipe 361, the second sleeve pipe 362 and the third sleeve pipe 363 from loosening in the housing 31, thus affecting the guiding effect.

The diameters of the first sleeve pipe 361, the second sleeve pipe 362 and the third sleeve pipe 363 may or may not be the same so long as they are adapted to produce a radial restraining effect on the inner members thereof, thus achieving the purpose of preventing buckling. Taking the first sleeve pipe 361 as an example, the bore diameter of the first sleeve pipe 361 may be slightly greater than the outer diameter of the push rod 13, such that when the push rod 13 is subjected to an axial pressing force and thus has a tendency of radial deflection, the first sleeve pipe 361 with a slightly bore diameter may prevent the radial deflection of the push rod 13, thereby achieving a better anti-buckling effect. It can be appreciated that, in other embodiments, the cannula may be disposed alternatively; for example, a cannula may be disposed only outside the control fiber and the traction fiber, but not disposed outside the push rod.

In some embodiments, the manipulation portion is further provided with a second limiting structure, the second limiting structure includes a telescopic sleeve. For example, a first telescopic sleeve pipe 371 is connected on the second manipulation portion 33; the first telescopic sleeve pipe 371 is coaxially sleeved between the traction fiber 22 and the second sleeve pipe; the proximal end of the first telescopic sleeve pipe 371 and the proximal end 22a of the traction fiber 22 are fixed to the second manipulation portion 33; the distal end of the first telescopic sleeve pipe 371 is inserted into the second sleeve pipe 362 and may move axially relative to the second sleeve pipe 362 under the action of the second manipulation portion 33. And during the movement of the second manipulation portion 33, the distal end of the first telescopic sleeve pipe 371 may not be exposed from the proximal end of the second sleeve pipe 362. In this embodiment, the first telescopic sleeve pipe 371 may be telescopically positioned between the traction fiber 22 and the second sleeve pipe 362 to further enhance the radial constraint on the traction fiber 22, thus effectively resisting buckling and maintaining the ability of the traction fiber 22 to move axially relative to the second sleeve pipe 362. In this configuration, the proximal end of the first telescopic sleeve pipe 371 and the proximal end of the traction fiber 22 are fixed on the second manipulation portion 33; and the distal end of the first telescopic sleeve pipe 371 is inserted into the second sleeve pipe 362. Thereby, when the second manipulation portion 33 drives the traction fiber 22 to move axially, the traction fiber 22 always gains the restraining effect of the first telescopic tube 371 in the radial direction. Therefore, even when the proximal end 22a of the traction fiber 22 stretches out a relatively long distance from the proximal end 362a of the second sleeve pipe 362, the traction fiber 22 is not easily radially deflected due to the radial constraint of the first telescopic sleeve pipe 371. Thereby, the traction fiber 22 may maintain a better axial movement performance under the axial telescopic movement between the first telescopic sleeve pipe 371 and the second sleeve pipe 362, thus enhancing the manipulation effect of the second manipulation portion 33 on the traction fiber 22.

In some embodiments, a second telescopic sleeve pipe 372 is connected on the third manipulation portion 34; the second telescopic sleeve pipe 372 is coaxially sleeved between the control fiber 23 and the third sleeve pipe. The proximal end of the second telescopic sleeve pipe 372 and the proximal end 23a of the control fiber 23 are fixed to the third manipulation portion 34, and the distal end of the second telescopic sleeve pipe 372 is inserted into the third sleeve pipe 363 and may move axially relative to the third sleeve pipe 363 under the action of the third manipulation portion 34. During the movement of the third manipulation portion 34, the distal end of the second telescopic sleeve pipe 372 is not exposed from the proximal end of the third sleeve pipe 363. The second telescopic sleeve pipe 372 is axially and telescopically inserted into the third sleeve pipe 363, thus being meeting the anti-buckling requirement when the control fiber 23 is pushed and pulled with a large stroke in an axial direction. In particular, the proximal end of the second telescopic sleeve pipe 372 is fixed to the third manipulation portion 34 together with the proximal end 23a of the control fiber 23, such that when the second manipulation portion 33 drives the control fiber 23 to move axially, the second telescopic sleeve pipe 372 always exerts a better radial restraining effect on the control fiber 23 to prevent the control fiber 23 from buckling.

It can be further understood that the diameter and length of the first and second telescopic sleeves 371 and 372 are adapted to the radial constraint requirements of the internal components thereof only. Taking the second telescopic sleeve pipe 372 as an example, the second telescopic sleeve pipe 372 is sleeved between the control fiber 23 and the third sleeve pipe 363, and the inner wall of the second telescopic sleeve pipe 372 may be closely coated on the control fiber 23, and may also form a certain gap with the outer wall of the control fiber 23. Accordingly, the inner wall of the third sleeve pipe 363 may be closely coated on the second telescopic sleeve pipe 372, and may also form a certain gap with the outer wall of the second telescopic sleeve pipe 372. The above configuration may not only maintain the smooth movement of the control fiber 23 and the second telescopic sleeve pipe 372 relative to the third sleeve pipe 363 in the axial direction, but also may limit the radial deflection of the control fiber 23 by the axial telescopic movement of the second telescopic tube 372 in the third sleeve pipe 363, thereby effectively ensuring that the control fiber 23 is free of buckling, and improving the manipulation reliability.

It can be appreciated that in this embodiment, the axial displacement distance of the first manipulation portion is smaller than that of the second manipulation portion and the third manipulation portion. Moreover, the outer diameter of the push rod is larger than that of the control fiber and the traction fiber. Therefore, other telescopic sleeves may be not disposed between the first sleeve pipe and the control fiber. That is to say, whether a sleeve pipe or a telescopic sleeve pipe is disposed according to the displacement distance and the outer diameter of the corresponding fiber or rod. A person skilled in the art may make corresponding changes, substitutions or choices according to actual situations.

It can be understood that in other embodiments, the limiting structure may also be a guide rail fixed on the inner wall of the housing, and the guide rail is provided with a groove or a through hole; and the elongated member is disposed in the groove or the through hole; alternatively, the limiting structure may be a part of the pipe body; the limiting structure forms a groove. That is, the cross section of the limiting structure is a section of arc, such that the elongated member is received within the groove.

In some embodiments, in combination with FIGS. 4 and 5, the first manipulation portion 32 includes a first sliding block 321 and a first pushing member 322. The first sliding block 321 is slidably disposed in the housing 31 and is connected to the proximal end 13a of the push rod 13; the first pushing member 322 is connected to the first sliding block 321, and partial structures of the first pushing member 322 are exposed to the housing 31; and the first pushing member 322 may move axially relative to the housing 31, such that the first sliding block 321 drives the push rod 13 to move axially.

Figure 6:
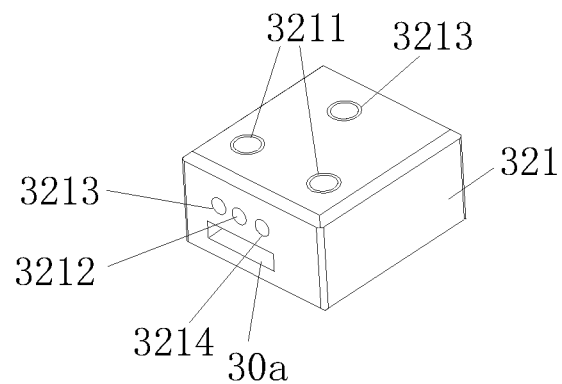
FIG. 6 is a schematic diagram illustrating a structure of a first sliding block of the control handle according to an embodiment.

In combination with FIG. 6, in some embodiments, the first sliding block 321 may be rectangular. In other embodiments, the first sliding block 321 may also be in other shapes, for example, the first sliding block 321 may be in a triangular or elliptical shape on a cross section perpendicular to the axial direction; the shape of the first sliding block 321 is not defined herein as long as the first sliding block 321 moves along the linear guide rail 380, thus driving the push rod 13 to move axially in the catheter body 11.

The first sliding block 321 is provided with one or more first connecting holes 3211 such that the first connecting hole 3211 is matched with connecting members, such as, a screw or a bolt, thus fixedly connecting the first pushing member 322 with the first sliding block 321.

The first sliding block 321 is provided with a first insertion hole 3212 extending in an axial direction, and a positioning hole 3213 communicating through the first insertion hole 3212 from a radial direction; the proximal end 13a of the push rod 13 is inserted into the first insertion hole 3212; and locking members, such as, a screw or a top thread, are fastened to the positioning hole 3213 and abutted against the proximal end 13a of the push rod 13 in the first insertion hole 3212, such that the proximal end 13a of the push rod 13 is fixedly connected on the first sliding block 321.

The second manipulation portion 33 and the third manipulation portion 34 are both located on one side where the proximal end of the first manipulation portion 32 is located; the first sliding block 321 is provided with a first through hole 3213 and a second through hole 3214 which extend in an axial direction. The second sleeve pipe 362 and the third sleeve pipe 363 are axially and movably disposed to pass through the first through hole 3213 and the second through hole 3214, respectively. Such a configuration mode achieves that the second sleeve pipe 362 is utilized to exert an anti-buckling effect on the traction fiber 22 and the third sleeve pipe 363 is utilized to exert an anti-buckling effect on the control fiber 23; and the second sleeve pipe 362 and the third sleeve pipe 363 may be axially and movably disposed to pass through the first sliding block 321 of the first manipulation portion 32, not interfering with the axial movement of the first sliding block 321.

It can be appreciated that the second sleeve pipe 362 and the third sleeve pipe 363 may be disposed axially and movably to pass through the first sliding block 321 of the first manipulating portion 32, such that when the push rod 13 is driven by the first sliding block 321 to move axially in the catheter body 11, the second sleeve pipe 362 and the third sleeve pipe 363 may always be supported by the first sliding block 321, thus obtaining axial stability. Accordingly, the second sleeve pipe 362 may have a better guiding effect on the traction fiber 22 in the axial direction so as to prevent the traction fiber 22 from deviating radially. Correspondingly, the third sleeve pipe 363 may have a better guiding effect on the control fiber 23 in the axial direction so as to prevent the control fiber 23 from deviating radially.

The second manipulating portion 33 and the third manipulating portion 34 are sequentially disposed in the axial direction on the side where the proximal end of the first manipulating portion 32 is located.

In this embodiment, the second manipulation portion 33 includes a second sliding block 331 and a second pushing member 332; the second sliding block 331 is slidably disposed in the housing 31 and is connected to the proximal end 22a of the traction fiber 22; the second pushing member 332 is connected to the second sliding block 331, and partial structures of the second pushing member 332 are exposed to the housing 31, and the second pushing member 332 may move axially relative to the housing 31, such that the traction fiber 22 is driven by the second sliding block 331 to move axially.

In combination with FIGS. 4 and 5, a linear guide rail 380 is fixedly disposed in the housing 31, and the first sliding block 321 and the second sliding block 331 are slidably disposed on the linear guide rail 380. For example, the first sliding block 321 and the second sliding block 331 are both provided with a sliding groove or a sliding hole 30a in sliding fit with the linear guide rail 380, such that the linear guide rail 380 is slidably disposed to pass through the sliding groove or the sliding hole 30a. The above configuration may achieve the sliding fit of the first sliding block 321 and the second sliding block 331 with the linear guide rail 380. Understandably, since the first sliding block 321 is required to drive the push rod 13 to move axially and the second sliding block 331 is required to drive the traction fiber 22 to move axially, the linear guide rail 380 is substantially axially disposed in the housing 31.

The sliding groove or sliding hole 30a may be rectangular or triangular in the cross section perpendicular to an axial direction, or "I"-shaped. Accordingly, the linear guide rail 380 has a structural form adapted to the sliding groove or sliding hole 30a, which will not be described in detail herein.

Figure 7:
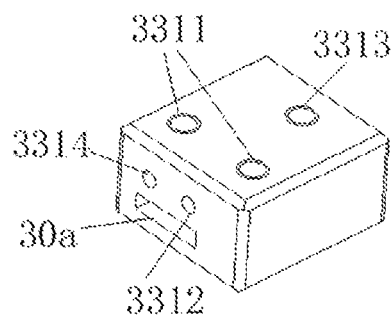
FIG. 7 is a schematic diagram illustrating a structure of a second sliding block of the control handle according to an embodiment.

The second sliding block 331 has a structure similar to that of the first sliding block 321. For example, in combination with FIG. 7, in some embodiments, the second sliding block 331 may be rectangular. In other embodiments, the second sliding block 331 may also be in other shapes. For example, the second sliding block 331 may be in a triangular or elliptical shape on the cross section perpendicular to an axial direction. The shape of the second sliding block 331 is not defined here provided that the second sliding block 331 may move along the linear guide rail 380 to drive the traction fiber 22 to move axially in the catheter body 11.

The second sliding block 331 is provided with one or more second connecting holes 3311, such that the second connecting hole 3311 is matched with connecting members, such as, a screw or a bolt, thus fixedly connecting the second pushing member 332 with the second sliding block 331. Accordingly, the second sliding block 331 is provided with a second insertion hole 3312 extending in an axial direction, and a locking hole 3313 penetrating and communicating with the second insertion hole 3312 in a radial direction. The proximal end 22a of the traction fiber 22 and the proximal end of the first telescopic sleeve pipe 371 are inserted into the second insertion hole 3312; locking members, such as, a screw or a top thread, are fastened to the locking hole 3313 and abutted against the traction fiber 22 and the first telescopic sleeve pipe 371 in the second insertion hole 3312, such that the proximal end 22a of the traction fiber 22 and the proximal end of the first telescopic sleeve pipe 371 are fixedly connected on the second sliding block 331.

It can be understood that in some embodiments, the first telescopic sleeve pipe 371 outside the traction fiber 22 may be omitted, i. e., the first telescopic sleeve pipe 371 need not be connected on the second sliding block 331, such that the traction fiber 22 may be disposed directly to pass through the second sleeve pipe 362. And in this case, the locking member may be engaged with the locking hole 3313 in threaded fit and abutted against the proximal end 22a of the traction fiber 22, such that the second sliding block 331 manipulates the traction fiber 22 to move axially in the catheter body 11 under the action of the second pushing member 332.

The second sliding block 331 is provided with a third through hole 3314, and the third sleeve pipe 363 may be axially disposed to pass through the third through hole 3314 movably, such that the control fiber 23 disposed to pass through the third sleeve pipe 363 may pass through the second sliding block 331, and the proximal end 23a of the control fiber 23 is connected to the third manipulation portion 34. Further, the second sliding block 331 may move axially relative to the third sleeve pipe 363, such that the second sliding block 331 is not interfered by the third sleeve pipe 363 when driving the traction fiber 22 to move axially.

It may be understood that the third sleeve pipe 363 is always disposed to pass through the third through hole 3314 during the movement of the second sliding block 331, such that the third sleeve pipe 363 is utilized to exert a better axial guiding effect on the control fiber 23, thus preventing the control fiber 23 from being pressed and bent.

In some embodiments, a clamping structure is disposed at the sliding fit portion between the first sliding block 321 and the linear guide rail 380, and/or, the sliding fit portion between the second sliding block 331 and the linear guide rail 380, such that the clamping structure may exert a better effect of prompting being in place, thereby making the manipulation simpler when the first sliding block 321 or the second sliding block 331 slides to the corresponding position.

A clamping structure between the first sliding block 321 and the linear guide rail 380 is merely set as an example for description.

Figure 8:
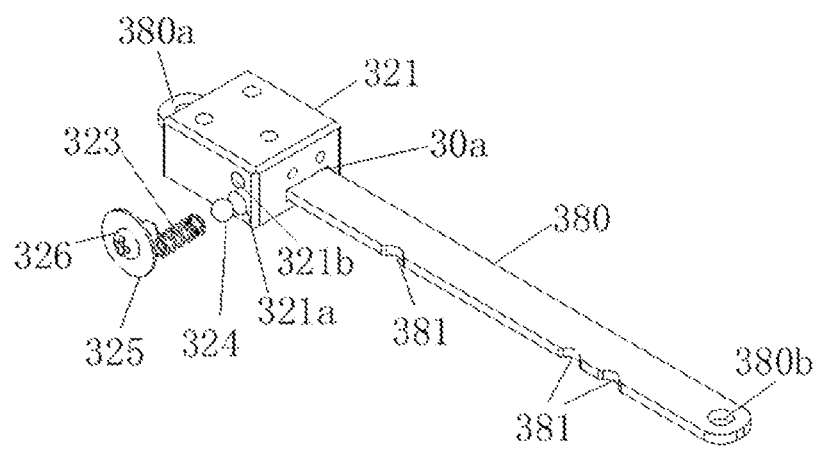
FIG. 8 is a schematic diagram illustrating a cooperation structure of the first sliding block and a linear guide rail in the control handle according to an embodiment.

In combination with FIG. 8, one or more arc-shaped grooves 381 are disposed on the side of the linear guide rail 380; an elastic member 323 and a ball 324 are disposed in the first sliding block 321; the ball 324 is elastically abutted on one side of the linear guide rail 380 provided with the arc-shaped groove 381 under the action of the elastic member 323. When the first sliding block 321 moves along the linear guide rail 380 until the ball 324 is opposite to the arc-shaped groove 381, partial structures of the ball 324 are abutted into the arc-shaped groove 381. Therefore, a sound is generated due to the impact between the ball 324 and the linear guide rail 380 at the arc-shaped groove 381 once the ball 324 is abutted into the arc-shaped groove 381, thus exerting a better effect of prompting being in place, achieving simple operation and avoiding poor effect caused by insufficient manipulation or over-manipulation. In addition, the opening on the housing may exert the limiting effect in axial length, and may prompt the maximum movement limit for the operator better in coordination with the sound feedback effect of the elastic member and the ball.

Accordingly, the above clamping structure may be configured by the second sliding block 331 and the linear guide rail 380 directly, so as to prompt the second sliding block 331 being positioned in place, which will not be described in detail herein.

It may be understood that the number and position of the arc-shaped grooves 381 on the linear guide rail 380 may be configured according to the positioning requirements of the first sliding block 321 and/or the second sliding block 331. For example, in some embodiments, as shown in FIG. 8, two arc-shaped grooves 381 are respectively disposed at the proximal end 380a and the distal end 380b of the linear guide rail 380 in the extension direction thereof; and an arc-shaped groove 381 is disposed in the middle, such that when the first sliding block 321 moves towards the distal end 380a along the linear guide rail 380 to be opposite to the arc-shaped groove 381 at the distal end 380a. Since the ball 324 disposed in the first sliding block 321 will make an impact sound when the ball 324 is clamped into the arc-shaped groove 381 under the elastic force of the elastic member 323, which may exert a prompt effect when the first sliding block 321 slides to the distal end 380a of the linear guide rail 380. Accordingly, when the second sliding block 331 moves toward the proximal end 380b along the linear guide rail 380 to be opposite to the arc-shaped groove 381 at the proximal end, the ball 324 disposed in the second sliding block 331 is clamped into the arc-shaped groove 381 located at the proximal end 380b. The above configuration also may exert a prompt effect when the second sliding block 331 slides relative to the linear guide rail 380.

The elastic member 323 may be a spring, or may be an elastic bar or rod made of an elastic material.

The prompt of being in place may be achieved between the first sliding block 321/the second sliding block 331 and the linear guide rail 380 by a same structural form.

An assembly structure between the first sliding block 321 and the linear guide rail 380 is merely set as an example to further describe the mounting forms of the elastic member 323 and the ball 324.

With continuing reference to FIG. 8, a through hole 321a is disposed on the side wall of the first sliding block 321; the through hole 321a penetrates to the side wall of a sliding hole 30a of the first sliding block 321; and the elastic member 323 is abutted against and communicated with the ball 324 to be mounted into the through hole 321a together, such that the ball 324 is abutted to the linear guide rail 380 in sliding fit with the sliding hole 30a. A stopping member, such as, a spacer 325 or a baffle, is disposed on a side wall of the first sliding block 321 opened with the through hole 321a, thus positioning the elastic member 323, thereby preventing the elastic member 323 from being withdrawn from the through hole 321a.

A spacer 325 is taken as a stopping member as an example, and the spacer 325 is locked to a mounting hole location 321b on the first sliding block 321 via connecting members 326, such as a screw or a bolt. The spacer 325 covers the through hole 321a and is abutted against the elastic member 323. Then, the elastic member 323 is in a compressed state and the ball 324 is elastically abutted against the linear guide rail 380. Further, when the first sliding block 321 moves relative to the linear guide rail 380 such that the ball 324 is opposite to the arc-shaped groove 381, the ball 324 is abutted into the arc-shaped groove 381 under the elastic force of the elastic member 323 to make a sound, thus prompting that the first sliding block 321 slides in position along the linear guide rail 380. That is, the push rod 13 is driven by the first sliding block 321 to manipulate the opening or closure of the grasping portion 12.

In other embodiments, the stopping member may be also fixed on the side wall of the first sliding block 321 which is opened with the through hole 321a by welding or gluing, and abutted against an end portion of the elastic member 323 close to the outside of the through hole 321a, thus limiting the elastic member 323 to be popped out from the through hole 321a.

In combination with FIGS. 3 to 5, a conductive sliding rail 390 is fixedly disposed in the housing 31, and the proximal end of the conductive sliding rail 390 is connected to a conductive interface (not shown) at a proximal end portion of the housing. The third manipulation portion 34 is slidably connected to the conductive sliding rail 390, i. e., the third manipulation portion 34 may move axially relative to the conductive sliding rail 390. A conductive elastic piece 343 is disposed at a sliding connection portion between the third operation manipulation portion 34 and the conductive sliding rail 390; the conductive elastic piece 343 is fixedly connected to the third manipulation portion 34; and when the third manipulation portion 34 slides along the conductive sliding rail 390, the conductive elastic piece 343 keeps elastically abutted against the conductive sliding rail 390. For example, the third manipulation portion 34 includes a third sliding block 341 and a third pushing member 342. The third sliding block 341 is slidably disposed on the conductive sliding rail 390 and connected to the proximal end 23a of the control fiber 23, and a third pushing member 342 is connected to the third sliding block 341. Partial structures of the third pushing member 342 are exposed to the housing 31 so as to manipulate the third pushing member 342; the third pushing member 342 may move axially relative to the housing 31, such that the third sliding block 341 drives the control fiber 23 to move axially; a conductive elastic piece 343 is disposed at the sliding connection portion of the third sliding block 341 and the conductive sliding rail 390, and the conductive elastic piece is fixedly connected to the third sliding block. When the third manipulation portion 34 slides along the conductive sliding rail 390, the conductive elastic piece 343 keeps abutted against the conductive sliding rail 390, such that the conductive elastic piece 343 always maintains electric contact with the conductive sliding rail 390, thus meeting the power supply requirements of the cutting device 20.

Figure 9:
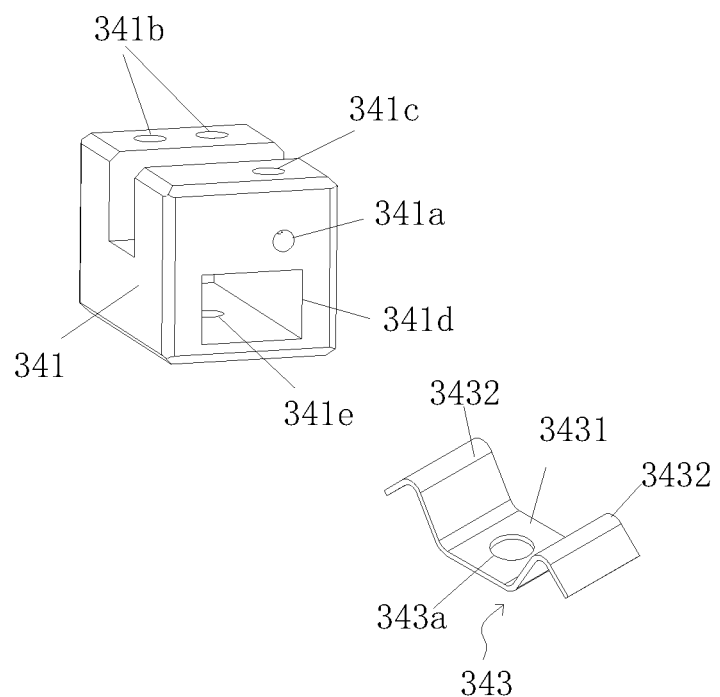
FIG. 9 is a schematic diagram illustrating a structure of a third sliding block and a conductive elastic piece in the control handle according to an embodiment.

In combination with FIG. 9, the third sliding block 341 has a cuboid structure. In other embodiments, the third sliding block 341 may be in other shapes, for example, the third sliding block 341 is in a triangular or elliptical shape in the cross section perpendicular to an axial direction. The shape of the third sliding block 341 is not defined here as long as the third sliding block 341 may move along the conductive sliding rail 390, thus driving the control fiber 23 to move axially in the catheter body 11.

The third sliding block 341 has an axially extending through hole 341a having an inner diameter slightly larger than an outer diameter of the second telescopic sleeve pipe 372, such that the second telescopic sleeve pipe 372 is inserted into the through hole 341a. The third sliding block 341 further has a first threaded hole 341b and a second threaded hole 341c.

The first threaded hole 341b is configured for cooperating with connecting members, such as, a screw or a bolt, such that the third sliding block 341 is fixedly connected with the third pushing member 342. The number and the position of the first threaded holes 341b on the third sliding block 341 may be reasonably configured according to the connection requirements of the third sliding block 341 and the third pushing member 342, which is not defined here.

The second threaded hole 341c is orthogonal to the position of the through hole 341a. After the proximal end of the second telescopic sleeve pipe 372 and the proximal end of the control fiber 23 located therein are inserted into the through hole 341a, fasteners, such as, a screw or a top thread are threadedly engaged at the second threaded hole and abutted against the proximal end of the second telescopic sleeve pipe 372 and the proximal end 23a of the control fiber 23, such that the proximal end of the second telescopic sleeve pipe 372 and the proximal end of the control fiber 23 are fixed connected with the third sliding block 341.

It may be understood that, in some embodiments, the second telescopic sleeve pipe 372 may be omitted, namely, the control fiber 23 is directly disposed to pass through the third sleeve pipe 363. At this time, the fastener is threadedly engaged at the second threaded hole 341c, abutted against the proximal end 23a of the control fiber 23 inserted into the through hole 341a, such that the control fiber 23 is connected with the third sliding block 341. Furthermore, the third sliding block 341 may manipulate the control fiber 23 to move axially in the catheter body 11 under the action of the third pushing member 342.

With continuing reference to FIG. 9, the third sliding block 341 further has a square through hole 341d having a size much greater than the size of the cross section of the conductive sliding rail 390, such that the third sliding block 341 has sufficient mounting space to arrange the conductive elastic piece 343 when the third sliding block 341 is slidingly engaged with the conductive sliding rail 390 through the square through hole 341d.

For example, a mounting hole 341e is opened on a side wall of the square through hole 341d on the third sliding block 341; the conductive elastic piece 343 has a connecting portion 3431 provided with a through hole 343a, and the conductive elastic piece 343 is mounted into the square through hole 341d. Connecting members, such as a screw or bolt, pass through the through hole 343a of the conductive elastic piece 343 and are fixed on the mounting hole 341e, such that the conductive elastic piece 343 is fixedly connected with the third sliding block 341. It may also be understood that in this embodiment, since the control fiber 23 is not in direct contact with the conductive elastic piece 343 or the conductive sliding rail 390, the third sliding block 341 should be made of a conductive material. It can be appreciated that in other embodiments, when the control fiber is directly connected to a conductive elastic piece or a conductive sliding rail, or indirectly connected via other electric conductors, the third sliding block is no longer limited to being made of a conductive material.

In other embodiments, the conductive elastic piece 343 may also be fixed at the square through hole 341d of the third sliding block 341 by welding, glue bonding or buckle connection, or the like only when the conductive sliding rail 390 is in sliding fit with the third sliding block 341, the conductive elastic piece 343 is in elastic contact with the conductive sliding rail 390, thus achieving an electric connection therebetween.

The conductive elastic piece 343 has one or two elastic abutting portions 3432 bent and projected by the connecting portion 3431, such that when the conductive sliding rail 390 is assembled into the square through hole 341d of the third sliding block 341, the elastic abutting portions 3432 are elastically abutted against and keep an electric contact with the conductive sliding rail 390. Therefore, when the third sliding block 341 moves along the conductive sliding rail 390, the conductive elastic piece 343 still keeps a good electric contact with the conductive sliding rail 390, so as to meet the power supply requirements of the cutting device 20.

The elastic abutting portion 3432 is "V"-shaped or "U"-shaped so as to maintain a line contact or a surface contact with the conductive sliding rail 390, thus obtaining a better electric contact effect. Meanwhile, the above configuration reduces the sliding friction of the conductive elastic piece 343 during the movement of the third sliding block 341 relative to the conductive sliding rail 390 so as to avoid abrasion, thereby ensuring stable electric contact between the conductive elastic piece 343 and the conductive sliding rail 390.

In other embodiments, the structure where the third sliding block 341 is in sliding fit with the conductive sliding rail 390 may not be a square through hole 341. For example, if the conductive sliding rail 390 is an I-shaped guide rail, the structure where the third sliding block 341 is in fit connection with the conductive sliding rail 390 may be a sliding groove with an I-shaped cross section. For another example, if the conductive sliding rail 390 has a triangular cross section, the sliding groove where the third sliding block 341 is in fit connection with the conductive sliding rail 390 has a triangular cross section.

It may be understood that the conductive elastic piece 343 and the conductive sliding rail 390 may be made of easily conductive metal materials such as, iron, aluminum, copper. But the material of the conductive elastic piece 343 is not limited herein as long as the conductive elastic piece 343 may be in electric contact with the conductive sliding rail 390 so as to meet the power supply requirements of the cutting device 20.

A conductive structure is disposed in the housing, and when the conductive interface at the proximal end of the housing is powered on, it may be ensured that the third sliding block is also always in a powered state, thus avoiding the failure of cutting caused by the invalid electric connection when cutting tissues.

It can be appreciated that in other embodiments, the electric connection between the conductive sliding rail and the third sliding block may also be implemented by other conductive structures as long as it is ensured that the third sliding block is always electrically connected to the conductive structure during sliding process. For example, an electric brush may be disposed on the third sliding block, and the electric brush is always in contact with the surface of the conductive sliding rail; alternatively, the conductive structure may include a spring; the spring may be disposed at a position where the third sliding block is electrically connected to the conductive sliding rail; one end of the spring is fixedly connected to the third sliding block and always in a compressed state.

It can also be appreciated that in other embodiments, the conductive sliding rail may not be provided, i. e., the third sliding block is directly connected to the conductive interface at the proximal end of the housing via the conductive structure.

In the embodiments, the configuration of a limiting structure for limiting the elongated member to prevent the elongated member from buckling, an opening on the housing for limiting the axial movement range of the manipulation portion, and an elastic member and a ball for prompting the movement in place, a conductive structure for ensuring that the third manipulation portion is always powered on during the movement is to ensure that the neostomy apparatus is valid in each operation process of the neostomy apparatus in use, such that the grasping device may successfully grasp the tissue, and the cutting device may also successfully cut the tissue.

Each feature of the above embodiments may be in any combination. To make the description concise, all the possible combinations of each feature in the above embodiments are not described one by one. However, any combination of these features shall fall within the scope of the embodiments as long as there is no contradiction therebetween.

The above examples are merely illustrative of several embodiments of the embodiments, and are described in greater detail, but are not construed as limiting the embodiments. It is understood that any person skilled in the art may further make several variations and modifications within the concept of the embodiments, and these variations and modifications fall within the scope of the embodiments.

The invention claimed is:

1. A neostomy apparatus, comprising: a grasping device, a cutting device and a control handle; the control handle comprises a housing and a manipulation portion disposed in the housing, the manipulation portion is configured to axially move relative to the housing; the grasping device or the cutting device comprises an elongated member, and the manipulation portion drives the elongated member to move axially; the elongated member is partially located in the housing, and a first limiting structure is further disposed in the housing, the first limiting structure has a groove or a through hole, and a portion of the elongated member located in the housing is at least partially disposed in the groove or the through hole of the first limiting structure, the elongated member is configured to axially move relative to the first limiting structure; and the elongated member resists bending due to the radial constraint of the first limiting structure;

wherein the grasping device further comprises a catheter body, the elongated member passing through the catheter body;

wherein the elongated member comprises a push rod, a traction fiber, and a control fiber;

wherein the manipulation portion comprises a first manipulation portion, a second manipulation portion, and a third manipulation portion;

wherein the first manipulation portion, the second manipulation portion, the third manipulation portion are configured to manipulate an axial movement of the push rod, the traction fiber, and the control fiber in the catheter body, respectively;

wherein the cutting device comprises a cutting portion, the cutting portion being connected to distal ends of the traction fiber and the control fiber; and wherein the traction fiber and the control fiber are symmetrically disposed on a wall of the catheter body to exert opposite axial push-pull forces on the cutting portion.

2. The neostomy apparatus according to claim 1, wherein the first limiting structure comprises a first sleeve pipe, a second sleeve pipe, and a third sleeve pipe, which correspond to the first manipulation portion, the second manipulation portion and the third manipulation portion, respectively; wherein a proximal end of each of the first sleeve pipe, the second sleeve pipe, and the third sleeve pipe is close to a distal end of the corresponding first manipulation portion, second manipulation portion, and third manipulation portion, respectively.

3. The neostomy apparatus according to claim 1, wherein a proximal end of the catheter body is connected to the housing; the housing is provided with a sealing assembly; the sealing assembly is located at a distal end of the housing and is sealingly connected to the proximal end of the catheter body, and the catheter body is configured to be communicated with a negative pressure source through the sealing assembly, such that a negative pressure is formed in the catheter body under the action of the negative pressure source.

4. The neostomy apparatus according to claim 3, wherein the sealing assembly comprises a hollow pipe body and a sealing member connected at both ends of the hollow pipe body; a vent hole is opened on a side wall of the hollow pipe body, and the negative pressure source is communicated with the vent hole via a hose.

5. The neostomy apparatus according to claim 1, wherein, the second manipulation portion or the third manipulation portion is connected with a second limiting structure; the second limiting structure is configured to receive the elongated member and is coaxial with the first limiting structure; a proximal end of the second limiting structure and a proximal end of the elongated member are fixed on the second manipulation portion or the third manipulation portion; a distal end of the second limiting structure is inserted into the groove or the through hole of the first limiting structure and is configured to move axially relative to the first limiting structure under the action of the second manipulation portion or the third manipulation portion.

6. The neostomy apparatus according to claim 1, wherein a linear guide rail is fixedly disposed in the housing; the first manipulation portion and the second manipulation portion are slidably disposed on the linear guide rail; one or more arc-shaped grooves are disposed on a side of the linear guide rail; each of the first manipulation portion and the second manipulation portion comprises an elastic member and a ball; the ball is elastically abutted against one side of the linear guide rail opened with the arc-shaped groove under the action of the elastic member; and, when each of the first manipulation portion and the second moves along the linear guide rail until the ball is opposite to the arc-shaped groove, partial structures of the ball are abutted against the arc-shaped groove.

7. The neostomy apparatus according to claim 1, further comprising a conductive structure and a conductive interface disposed at a proximal end portion of the housing; the conductive structure always keeps electric connection with the third manipulation portion and the conductive interface when the third manipulation portion moves axially.

8. The neostomy apparatus according to claim 7, wherein the housing is provided with a conductive sliding rail, and a proximal end of the conductive sliding rail is connected to the conductive structure; and the third manipulation portion is slidably connected to the conductive sliding rail, and the third manipulation portion is configured to move axially relative to the conductive sliding rail.

9. The neostomy apparatus according to claim 8, wherein the conductive structure comprises a conductive elastic piece, and the conductive elastic piece is disposed at a sliding connection portion between the third manipulation portion and the conductive sliding rail; when the third manipulation portion moves axially along the conductive sliding rail, the conductive elastic piece is always abutted against the conductive sliding rail.

10. The neostomy apparatus according to claim 1, wherein each of the first manipulation portion, the second manipulation portion, and the third manipulation portion comprises a sliding block and a pushing member, and the sliding block is slidably disposed in the housing and is connected to the proximal end of the elongated member; the pushing member is connected to the sliding block, and partial structures of the pushing member are exposed to the housing, and the pushing member is configured to move axially relative to the housing, such that the sliding block drives the elongated member to move axially.

11. The neostomy apparatus according to claim 1, wherein the cutting device comprises a cutting portion, the cutting portion being connected to distal ends of the traction fiber and the control fiber; and wherein the traction fiber and the control fiber are symmetrically disposed on a wall of the catheter body to exert opposite axial push-pull forces on the cutting portion.

12. The neostomy apparatus according to claim 11, wherein the first manipulation portion is connected to the proximal end of the push rod and is configured for driving the push rod to move axially relative to the catheter body.

13. The neostomy apparatus according to claim 12, wherein the second manipulation portion is connected to the proximal end of the traction fiber and is configured for driving the traction fiber to move axially in the catheter body.

14. The neostomy apparatus according to claim 13, the third manipulation portion is connected with the proximal end of the control fiber and is configured for driving the control fiber to move axially in the catheter body.

15. The neostomy apparatus according to claim 2, wherein the push rod is configured to axially move relative to the first sleeve pipe; and wherein the traction fiber is configured to axially move relative to the second sleeve pipe, and wherein the control fiber is configured to axially move relative to the third sleeve pipe.

16. The neostomy apparatus according to claim 2, wherein the first manipulation portion comprises a first sliding block and a first pushing member, and the first sliding block is slidably disposed in the housing and is connected to the proximal end of the push rod; the first pushing member is connected to the first sliding block, and partial structures of the first pushing member are exposed to the housing; and the first pushing member is configured to move axially relative to the housing, such that the first sliding block drives the push rod to move axially.

17. The neostomy apparatus according to claim 16, wherein the second manipulation portion and the third manipulation portion are both located on one side where the proximal end of the first manipulation portion is located; the first sliding block is provided with a first through hole and a second through hole which extend in an axial direction; wherein the second sleeve pipe and the third sleeve pipe are axially and movably disposed to pass through the first through hole and the second through hole, respectively.

18. The neostomy apparatus according to claim 16, wherein the second manipulation portion comprises a second sliding block and a second pushing member, and the second sliding block is slidably disposed in the housing and is connected to the proximal end of the traction fiber; the second pushing member is connected to the second sliding block, and partial structures of the second pushing member are exposed to the housing, and the second pushing member is configured to move axially relative to the housing, such that the traction fiber is driven by the second sliding block to move axially.

19. The neostomy apparatus according to claim 18, wherein the second sliding block comprises a third through hole, and the third sleeve pipe is configured to move axially relative to the third through hole.

20. The neostomy apparatus according to claim 18, wherein the housing is provided with a conductive sliding rail, and the proximal end of the conductive sliding rail is connected to the conductive interface at a proximal end portion of the housing, the third manipulation portion is slidably connected to the conductive sliding rail, and the third manipulation portion is configured to move axially relative to the conductive sliding rail; wherein the third manipulation portion comprises a third sliding block and a third pushing member, and the third sliding block is slidably disposed on the conductive sliding rail and connected to the proximal end of the control fiber; the third pushing member is connected to the third sliding block, and partial structures of the third pushing member are exposed to the housing; the third pushing member is configured to move axially relative to the housing, such that the third sliding block drives the control fiber to move axially; wherein a conductive elastic piece is disposed at the sliding connection portion of the third sliding block and the conductive sliding rail, and the conductive elastic piece is fixedly connected to the third sliding block.

* * * * *